(12) United States Patent
Cannon

(10) Patent No.: US 7,329,120 B1
(45) Date of Patent: Feb. 12, 2008

(54) ORTHODONTIC BRACKET WITH VERTICAL SLOT AND METHOD OF USING SAME

(76) Inventor: James L. Cannon, 5297 Cleveland Hwy., Clermont, GA (US) 30527

( * ) Notice: Subject to any disclaimer, the term of this patent is extended or adjusted under 35 U.S.C. 154(b) by 261 days.

(21) Appl. No.: 10/972,977

(22) Filed: Oct. 25, 2004

(51) Int. Cl.
*A61C 3/00* (2006.01)
(52) U.S. Cl. .......................... 433/10; 433/15
(58) Field of Classification Search ............ 433/8, 433/10–15, 9
See application file for complete search history.

(56) References Cited

U.S. PATENT DOCUMENTS

| | | | |
|---|---|---|---|
| 3,163,933 A | 1/1965 | Begg et al. | |
| 3,178,821 A | 4/1965 | Kesling | |
| 3,178,822 A | 4/1965 | Fogel et al. | |
| 3,464,113 A * | 9/1969 | Silverman et al. | 433/11 |
| 3,748,740 A * | 7/1973 | Wildman | 433/11 |
| 3,835,539 A * | 9/1974 | Wallshein | 433/11 |
| 4,180,912 A * | 1/1980 | Kesling | 327/437 |
| 4,669,980 A * | 6/1987 | Degnan | 433/8 |
| 4,674,978 A * | 6/1987 | Acevedo | 433/8 |
| 5,037,297 A * | 8/1991 | Lerner | 433/14 |
| 5,059,119 A * | 10/1991 | Snead | 433/17 |
| 5,123,838 A | 6/1992 | Cannon | |
| 5,161,969 A * | 11/1992 | Pospisil et al. | 433/8 |
| 5,248,257 A | 9/1993 | Cannon | |
| 5,322,435 A * | 6/1994 | Pletcher | 433/11 |
| 6,071,119 A | 6/2000 | Christoff et al. | |
| 6,485,299 B1 | 11/2002 | Wildman | |
| 6,659,767 B2 | 12/2003 | Abels et al. | |
| 6,733,286 B2 | 5/2004 | Abels et al. | |
| 6,932,597 B2 | 8/2005 | Abels et al. | |
| 7,001,179 B2 | 2/2006 | Devincenzo | |
| 7,014,460 B2 | 3/2006 | Lai et al. | |
| 7,025,591 B1 | 4/2006 | Kesling | |
| 2004/0072119 A1 | 4/2004 | Voudouris | |
| 2004/0209219 A1 | 10/2004 | Miyaji et al. | |
| 2006/0014116 A1* | 1/2006 | Maijer et al. | 433/11 |
| 2006/0246392 A1 | 11/2006 | Vigolo | |

\* cited by examiner

*Primary Examiner*—Cary E. O'Connor
(74) *Attorney, Agent, or Firm*—King & Spalding

(57) ABSTRACT

There is disclosed an orthodontic bracket comprising a body member having a gingival opening mesio-distally extending slot formed therein. The slot is sized and shaped to receive an archwire. The body member also comprising a vertical leg between the slot and a labial or facial surface of the body member. The vertical leg defines a portion of the slot. The body member also comprises a shoulder attached to the vertical leg adjacent the opening and extending into the slot. A method of using a orthodontic bracket is also disclosed.

14 Claims, 2 Drawing Sheets

ORTHODONTIC BRACKET WITH VERTICAL SLOT AND METHOD OF USING SAME

FIELD OF THE INVENTION

The present invention relates generally to orthodontic brackets, and, more specifically, to an orthodontic bracket with a vertical archwire slot which most commonly opens toward the gingival. The present invention also includes an improved system for attaching or retaining an archwire in the vertical opening archwire slot.

BACKGROUND OF THE INVENTION

Orthodontic brackets which are applied to teeth, either by attachment to a band or by direct bonding to a tooth, for the purpose of applying a moving force to the tooth to which the bracket is attached are known in the art. The moving force is generated by a wire attached to similar brackets attached to adjoining teeth. The moving force applied to teeth over a period of time permits the movement of the teeth to accomplish desired alignment of the teeth.

There are two major bracket designs for applying this moving force currently employed in the orthodontic field. The most common bracket is a bracket that does not have a vertical archwire slot, but rather a relatively wide, 0.100 to 0.165 inch, rectangular horizontal archwire slot that opens to the facial side of the bracket. This slot is referred to as the edgewise slot. The edgewise slot has gained dominance, to a large extent, due to the ease of attaching or removing the archwire. The archwire is captured in the edgewise slot by a relatively small gauge stainless steel tie wire (ligature tie) or by a small donut-shaped retaining member made from resilient rubber-like material (O-ring). Both the ligature tie and the O-ring can be easily placed and removed.

The other bracket design is one that has a relatively narrow, 0.050 to 0.065 inch, vertical opening archwire slot. It most commonly opens to the gingival side. This slot is referred to as the lightwire slot. In prior art, the archwire is captured and secured in the lightwire slot by a brass pin having an elongated body portion and an enlarged head portion. The pin is inserted into a slot in the body of the bracket, and thereby captures the archwire between the head of the pin and the body of the bracket. The pin is then secured to the bracket by bending the elongated portion of the pin over the body of the bracket. An example of such a bracket is shown in U.S. Pat. No. 3,178,821 (the disclosure of which is incorporated herein by referenced).

The prior art method of securing archwires in the lightwire slot with a brass pin can be somewhat difficult; however, the removal of the pin in many cases can be extremely difficult. In prior art orthodontic bracket designs, an O-ring cannot be used to secure an archwire in the lightwire slot. Typically, the O-ring will stretch and the archwire may become disengaged from the lightwire slot. A ligature tie can be used to secure an archwire in the lightwire slot. However, the ligature tie forces the archwire into the bottom of the slot and thereby destroys the vertical dimension of the lightwire slot which is essential for the slot to function properly.

Both the edgewise slot and the lightwire slot have advantages under different circumstances. Furthermore, both slots might be used together or individually on the same patient. Therefore, in addition to orthodontic brackets with only the edgewise slot or only the lightwire slot, there have been developed combination brackets. Such combination brackets permit the use of either the edgewise slot or the lightwire slot individually or in unison within the same bracket. Examples of such combination brackets are shown in U.S. Pat. Nos. 3,178,822; 3,163,933; 5,123,838 and 5,248,257 (the disclosures of which are all incorporated herein by reference).

Accordingly, there is a need for an orthodontic bracket which provides a vertical opening archwire slot designed in such a way as to make it relatively easy to secure archwires in those slots. Furthermore, there is a need for an orthodontic bracket having a vertical opening archwire slot designed in such a fashion as to make it relatively easy to remove an archwire from such a slot.

SUMMARY OF THE INVENTION

The present invention satisfies the above-described needs by providing an orthodontic bracket comprising a body member having a gingival opening mesio-distally extending slot formed therein. The slot is sized and shaped to receive an archwire. The body member also comprising a vertical leg portion between the slot and a labial or facial surface of the body member. The vertical leg defines a portion of the slot. The body member also comprises a shoulder attached to the vertical leg member adjacent the opening and extending into the slot.

In an alternate embodiment, the present invention comprises a method of using an orthodontic bracket. The method comprises inserting an archwire in a gingival opening mesio-distally extending slot in an orthodontic bracket. A ligature is then wrapped around a vertical leg portion of the bracket between the slot and a facial surface such that the ligature is disposed in the slot between the archwire and a shoulder extending partially into the slot adjacent the opening. In a preferred embodiment, the ligature is wrapped around the vertical leg portion of the bracket at least twice whereby the ligature will not substantially rotate on the vertical leg portion.

Accordingly, it is an object of the present invention to provide an improved orthodontic bracket.

Another object of the present invention is to provide an improved method of securing or retaining an archwire in a vertical opening archwire slot in an orthodontic bracket.

A further object of the present invention is to provide an improved method of removing an archwire from a vertical opening archwire slot in an orthodontic bracket.

These and other objects, features and advantages of the present invention will become apparent upon reviewing the following detailed description of the disclosed embodiments and the appended drawing and claims.

DETAILED DESCRIPTION OF THE INVENTION

Figure 1:
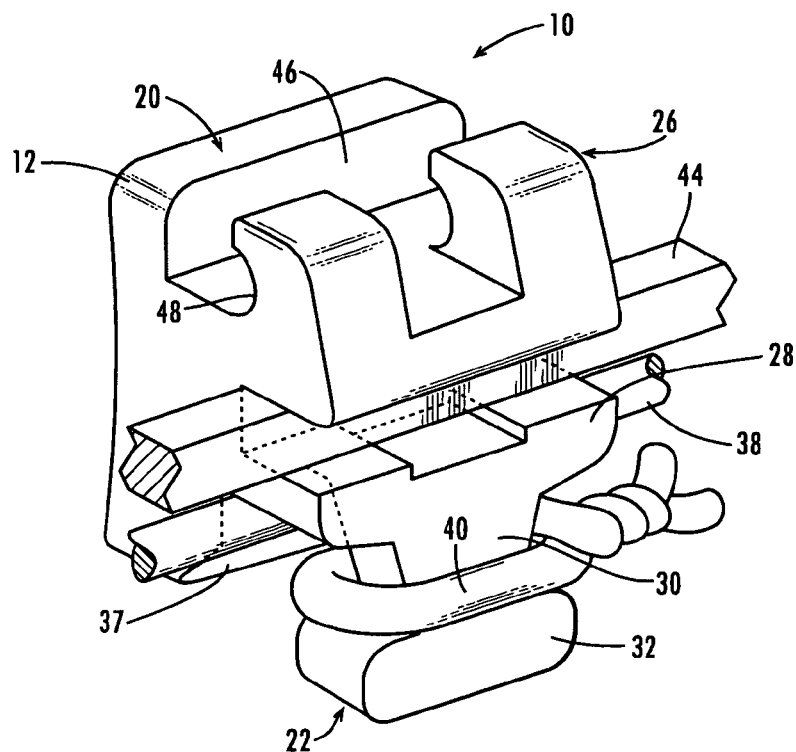
FIG. 1 is a perspective view of a disclosed embodiment of the orthodontic bracket of the present invention.

With reference to the drawing in which like numbers indicate like elements throughout the several views, it will be seen that there is an orthodontic bracket 10 in accordance with the present invention. The orthodontic bracket 10 is designed for temporary attachment to a tooth (not shown) using well known conventional adhesive or cementing techniques. The particular method used to attach the orthodontic bracket 10 to a tooth does not form a part of the present invention.

The orthodontic bracket 10 comprises a body member 12 made from a solid piece of surgical stainless steel or other suitable metal or plastic typically used in the orthodontic arts. The orthodontic bracket 10 can be made by machining a solid block of material, or, preferably, by casting using techniques well known in the art, such as the lost wax technique.

Figure 2:
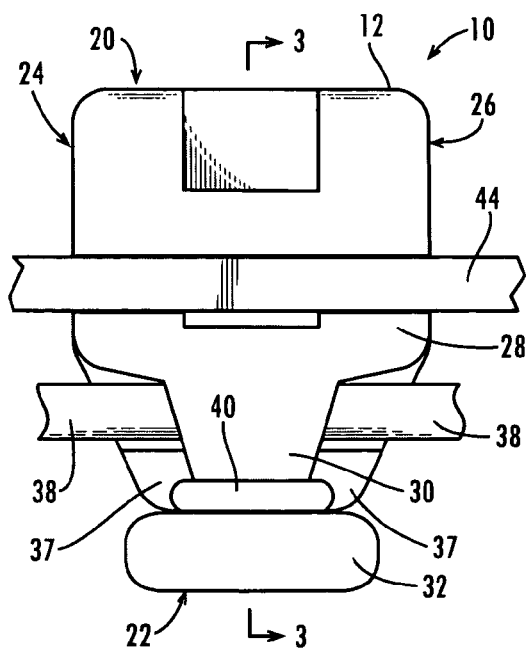
FIG. 2 is a front view of the orthodontic bracket shown in FIG. 1 showing archwires received in the archwire slots thereof and a ligature for retaining the archwire in the lightwire slot.

The body member 12 comprises a base portion 14 having a base surface 16. The base surface 16 is adapted for temporary attachment to a tooth (not shown). The body member 12 also has a labial or facial surface 18, an occlusal surface 20, a gingival surface 22, a left surface 24 and a right surface 26. The body member 12 further comprises a central portion 28 extending outwardly from said base portion 14 toward said facial surface 18. A vertical leg 30 extends vertically from the central portion 28 to said gingival surface 22. On the end of the vertical leg 30 distal from the central portion 28 is a shoulder 32. The shoulder 32 extends outwardly from the vertical leg 30 toward the base portion 14. The shoulder 32 also extends outwardly from the vertical leg 30 toward the left surface 24 and the right surface 26, as shown in FIG. 2. It is preferred that the tip of the vertical leg 30, including the shoulder 32, extends further in the gingival direction than the base portion 14. The vertical leg 30 is preferably tapered in the gingival direction; i.e., the vertical leg is wider (in the direction of the left surface 24 and right surface 26) where it joins the central portion 28 than where the vertical leg joins the shoulder 32 (FIG. 2).

The base portion 14, the central portion 28, the vertical leg 30 and the shoulder 32 define a lightwire slot 34 formed in the body member 12. The lightwire slot 34 includes an opening 36 in the gingival surface 22. The body member 14 includes a beveled corner 37 (FIGS. 2 and 3) so as to provide the desired opening 36 size between the shoulder 32 and the body member. In different terms, as shown in FIGS. 1-3, the orthodontic bracket 10 comprises a body member 14 having a gingival opening mesio-distally extending slot; i.e., lightwire slot 34, formed therein.

Received in the lightwire slot 34 is an archwire 38. The lightwire slot 34 and opening 36 are sized and shaped such that the archwire 38 may be easily inserted into the slot and removed from the slot. Preferably, the width of the opening 36 of the lightwire slot 34 is just slightly greater than the diameter of the archwire 38. With particular reference to FIGS. 2 and 3, there is shown a wire tie or ligature 40 disposed on the vertical leg 30 adjacent the shoulder 32. The ligature 40 is formed by wrapping a relatively small gauge surgical stainless steel wire around the vertical leg 30 and then twisting the free ends of the wire (not shown) together in a manner well known in the art. In a preferred embodiment, as shown in FIG. 4, the ligature 40 is formed by wrapping a relatively small gauge surgical stainless steel wire around the vertical leg 30 twice and then twisting the free ends of the wire (not shown) together.

Figure 3:
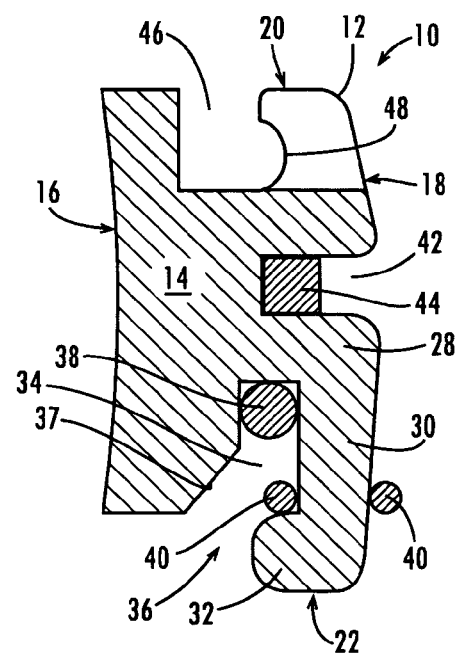
FIG. 3 is a cross-sectional view taken along the line 3-3 of the orthodontic bracket shown in FIG. 2.
Figure 4:
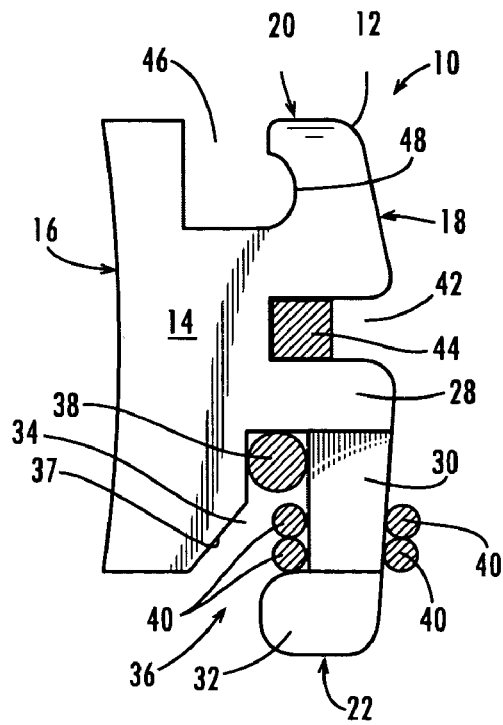
FIG. 4 is an alternate side view of the orthodontic bracket shown in FIG. 2 showing an archwire received in the lightwire slot thereof and a double-loop ligature for retaining the archwire in the lightwire slot.

In both FIGS. 3 and 4, it will be seen that the shoulder 32 prevents the ligature 40 from slipping off the end of the tapered vertical leg 30. The shoulder 32 therefore retains the ligature 40 in the lightwire slot 34. It will also be seen that when the ligature 40 is disposed in the lightwire slot 34, as shown in FIGS. 3 and 4, the ligature effectively reduces the diameter of the opening 36 of the slot to a size smaller than the diameter of the archwire 38. Therefore, when the ligature 40 is disposed in the lightwire slot 34, as shown in FIGS. 3 and 4, the archwire 38 cannot be removed or disengaged from the slot, either intentionally or under the influences of induced forces during wear of the bracket 10. Thus, the ligature 40 retains the archwire 38 in the lightwire slot 34.

It is specifically contemplated that the design of the bracket 10 of the present invention and the use of the ligature 40 has distinct advantages over the prior art in terms of its ability to retain archwires in the lightwire slot 34. In most, if not all, prior art brackets, when using a wire tie or ligature to retain an archwire in a lightwire slot, the ligature relies on tension as its retaining mechanism. That is, in prior art brackets, the archwire is lashed to the bracket by the ligature and the ligature is twisted tightly to hold the archwire in the slot. Since the ligature tie is made from a relatively small gauge steel having a relatively low tensile strength, when such wires are put under tension, as described above, they may tend to stretch causing the archwire to become disengaged from the lightwire slot or they may break. Broken ligatures are uncomfortable for the patient wearing them, and frequently require emergency repair.

In contrast with the prior art, the present invention does not rely on tension of a ligature to retain an archwire in the lightwire slot 34 of the bracket 10. As described above, the ligature 40 effectively reduces the size of the opening 36 to a size smaller than the diameter of the archwire 38, thereby preventing the archwire from being able to fit through the opening. Thus, when the archwire 38 tries to move out of the lightwire slot 34, the archwire contacts the ligature 40 which is captured between the archwire, the shoulder 32 and the vertical leg 30. Any removal force applied to the archwire 38 is therefore applied to the ligature 40 as a compressive force, not a stretching force. Since the compressive strength of the ligature 40 is relatively large compared to its tensile strength, the ligature will not tend to break when removal forces are applied to it by the archwire.

Either the single loop ligature 40, shown in FIG. 3, or the double loop ligature, as shown in FIG. 4, will provide the necessary retention of the archwire 38 in the lightwire slot 38. However, the double-loop ligature 40, shown in FIG. 4, is preferred. When a single-loop ligature 40, as shown in FIG. 3, is used, the single-loop may tend to rotate or spin around the vertical leg 30. When the ligature 40 can rotate or spin on the vertical leg 30, the twisted ends of the ligature may inadvertently moved to a position that pokes the lip or the gum of a wearer, thereby causing discomfort or injury for the wearer. As a part of the present invention, it has been discovered that when the double-loop ligature 40, as shown in FIG. 4, is used, the ligature is much less likely to rotate or spin on the vertical leg 30, thereby reducing the potential for discomfort or injury to the wearer.

Figure 5:
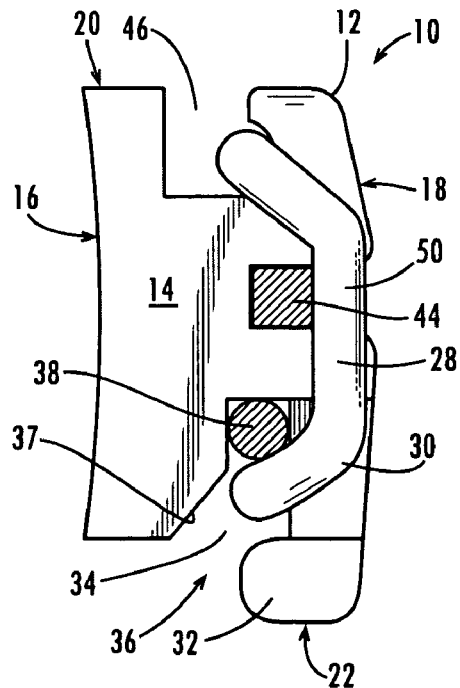
FIG. 5 is an alternate side view of the orthodontic bracket shown in FIG. 2 showing an archwire received in the lightwire slot thereof and an O-ring for retaining the archwire in the lightwire slot.

Although the bracket 10 of the present invention has been designed to provide particular advantages when using ligatures in the lightwire slot, the bracket is also designed to accommodate the edgewise technique and the use of conventional O-rings to retain archwires in their respective slots. As can best be seen in FIGS. 3-5, the bracket 10 of the present invention includes a conventional edgewise slot 42 formed in facial surface 18 of the body member 12. The edgewise slot 42 is sized and shaped to receive therein a conventional square archwire 44 (FIGS. 3-5).

The bracket 10 of the present invention will also accommodate the use of conventional O-rings or power chains (a series of O-rings). As best shown in FIGS. 3 and 4, a slot 46 is provided in the occlusal surface 20 of the body member 12. As best seen in FIG. 3, the slot 46 includes a hooked portion 48 for receiving an O-ring. As shown in FIG. 5, a conventional elastic orthodontic O-ring 50 is positioned in the hooked portion 48 of the slot 46, stretched over the archwire 44 and the other end of the O-ring is positioned in the lightwire slot 34. The O-ring 50 retains the archwire 38 in the lightwire slot in the same manner as the ligature 40 described above. Thus, when the archwire 38 tries to move out of the lightwire slot 34, the archwire contacts the O-ring 50 which is captured between the archwire, the shoulder 32 and the vertical leg 30. Any removal force applied to the archwire 38 is therefore applied to the O-ring 50 as a compressive force. The tension on the O-ring 50 also provides the retaining force for retaining the archwire 44 in the edgewise slot 42.

If it is desired to use a ligature to retain archwires in both the light wire slot 34 and the edgewise slot 42, a ligature may be wrapped around the vertical leg 30 in the same manner as described above. However, instead of twisting together the free ends of the ligature at this point, one of the free ends is stretched across the archwire 44, looped through the slot 46, brought back down across the archwire 44, and the free end of the ligature are then twisted together.

Use of the orthodontic bracket 10 of the present invention will now be considered. The orthodontic bracket 10 may be attached to a tooth (not shown) in a conventional manner by applying a suitable adhesive or cement to the base surface 16, and, then, applying the base surface to the surface of a tooth. The orthodontic bracket 10 may be applied to a tooth in either the upper arch or the lower arch. However, depending on which arch the tooth is located in, the orthodontic bracket 10 is oriented so that the gingival surface 22 is adjacent the wearer's gum.

After the orthodontic bracket 10 is attached to a tooth, an archwire 38 may be positioned in the lightwire slot 34. Optionally, an archwire 44, for use in the edgewise technique, may be positioned in the edgewise slot 42. The archwire 34 is then preferably secured in the lightwire slot 34 by securing a wire tie or ligature 40 around the vertical arm 30 adjacent the shoulder 32. The wire tie or ligature 40 is formed by wrapping a relatively small gauge wire around the vertical leg 30, and, then twisting the free ends of the wire together in a manner well known in the art. Wrapping the ligature 40 around the vertical arm 30 one time forms the single-loop ligature shown in FIG. 3. As a part of the present invention, it has been found that the single-loop ligature 40 may tend to rotate or spin on the vertical arm 30. Therefore, it is preferred, as a part of the present inventions, that the ligature 40 on the vertical arm 30 be formed as a double-loop, as shown in FIG. 4. The double-loop ligature is formed by wrapping the wire 40 around the vertical arm 30 twice. The free ends of the ligature 40 are then twisted together in a manner well known in the art. When the double-loop ligature 40 (FIG. 4) is used with the orthodontic bracket 10, the ligature is much less likely to rotate or spin on the vertical arm 30, and, therefore, is much safer and more comfortable to wear for the patient. Although it is preferred to wrap the ligature 40 around the vertical arm 30 twice, it is also contemplated that the ligature can be wrapped around the vertical arm more than twice, which will also prevent the ligature from rotating or spinning on the vertical arm.

The archwire 38 may also be retained in the lightwire slot 34 using a conventional orthodontic O-ring, instead of a wire tie or ligature. The archwire 38 is secured in the lightwire slot 34 by placing a portion of the O-ring 50 in the lightwire slot 34 adjacent the archwire, and, then, stretching the O-ring so that the other portion of the O-ring is disposed in the hook portion 48 of the slot 46.

Removal of the archwire 38 from the lightwire slot 34 is relatively easy. If a ligature 40 is used, the free ends of the ligature are untwisted or the wire is cut and the wire is unwrapped from the vertical arm 30. The archwire 38 can then be freely removed from the lightwire slot 34. If an O-ring 50 is used, the O-ring is stretched so that it can be removed from the slot 46. The other portion of the O-ring can then be withdrawn from the lightwire slot 34. The archwire 38 can then be freely removed from the lightwire slot 34.

It should be understood, of course, that the foregoing relates only to certain disclosed embodiments of the present invention and that numerous modifications or alterations may be made therein without departing from the spirit and scope of the invention as set forth in the appended claims.

What is claimed is:

1. A method of using an orthodontic bracket comprising:
   inserting an archwire in a vertical slot in said orthodontic bracket, said vertical slot being formed in said bracket intermediate a base surface and a labial surface of said bracket and having an opening on a gingival surface of said bracket; and
   wrapping a ligature around a vertical leg portion of said bracket between said vertical slot and said labial surface such that said ligature is disposed in said vertical slot between said archwire and a shoulder extending partially into said slot adjacent said opening.

2. The method of claim 1, wherein said ligature is wrapped around said vertical leg portion of said bracket at least twice.

3. A method of using an orthodontic bracket comprising:
   inserting an archwire in a gingival opening mesio-distally extending slot in said orthodontic bracket; and
   inserting a retaining member in said slot between said archwire and a shoulder extending partially into said slot adjacent said opening, such that said retaining member retains said archwire in said slot.

4. The method of claim 3, wherein said retaining member is an elastomeric retaining member.

5. A method of using an orthodontic bracket comprising:
   inserting an archwire in a vertical slot in said bracket, said vertical slot being formed in said bracket intermediate a base surface and a labial surface of said bracket and having an opening on a gingival surface of said bracket; and
   disposing a retaining member in said vertical slot such that said retaining member is disposed between said archwire and a shoulder extending partially into said slot adjacent said opening.

6. The method of claim 5, wherein said retaining member is an elastomeric retaining member.

7. The method of claim 5, wherein said retaining member is an O-ring.

8. The method of claim 5, wherein said retaining member is a power chain.

9. The method of claim 5, wherein said retaining member is a ligature.

10. An method comprising:
    inserting an archwire in a gingival opening mesio-distally extending slot formed in an orthodontic bracket, said orthodontic bracket including a shoulder extending partially into said slot; and disposing a retaining member in said slot between said archwire and said shoulder, said shoulder being sized and shaped such that when said retaining member is received in said slot between said archwire and said shoulder, said retaining member prevents removal of said archwire from said slot.

11. The method of claim 10, wherein said retaining member is an elastomeric retaining member.

12. The method of claim 10, wherein said retaining member is an O-ring.

13. The method of claim 10, wherein said retaining member is a power chain.

14. The method of claim 10, wherein said retaining member is a ligature.

* * * * *